United States Patent
Kolberg

[11] Patent Number: 6,161,364
[45] Date of Patent: Dec. 19, 2000

[54] TERMINAL STERILIZATION PROCESS FOR FILLED SYRINGES UNDER AN AUXILIARY PRESSURE

[75] Inventor: Reiner Kolberg, Berlin, Germany

[73] Assignee: Scherring Aktiengesellschaft, Berlin, Germany

[21] Appl. No.: 09/230,885

[22] PCT Filed: Aug. 1, 1997

[86] PCT No.: PCT/DE97/01671

§ 371 Date: Feb. 2, 1999

§ 102(e) Date: Feb. 2, 1999

[87] PCT Pub. No.: WO98/05366

PCT Pub. Date: Feb. 12, 1998

[30] Foreign Application Priority Data

Aug. 2, 1996 [DE] Germany .......................... 196 32 402

[51] Int. Cl.⁷ .................................................. B65B 55/02
[52] U.S. Cl. ............................... 53/425; 53/426; 53/432; 53/489; 53/510; 141/7; 141/18; 141/25; 141/59; 141/95; 141/198
[58] Field of Search ............................ 53/432, 510, 489, 53/426; 141/7, 25, 18, 27, 59, 198, 95

[56] References Cited

U.S. PATENT DOCUMENTS

| | | |
|---|---|---|
| 1,424,187 | 8/1922 | Seelman ................................. 215/248 |
| 4,628,969 | 12/1986 | Jurgens, Jr. et al. ....................... 141/1 |
| 5,207,983 | 5/1993 | Liebert et al. ............................. 422/25 |
| 5,531,255 | 7/1996 | Vacca ..................................... 141/285 |

FOREIGN PATENT DOCUMENTS

| | | |
|---|---|---|
| 94/13328 | 1/1994 | WIPO . |
| 95/00180 | 1/1995 | WIPO . |

*Primary Examiner*—Peter Vo
*Assistant Examiner*—Hemant M. Desai

[57] ABSTRACT

A production process for a prefilled, sterile syringe comprising providing a sterilized syringe barrel having sealable proximal and sealable distal ends. The proximal end being opened and the distal end being closed and adapted for coupling with a syringe outlet piece. In accordance with the process, the distal end of the barrel is closed and the barrel is then filled through the proximal end while the proximal end is opened with a fluid medium in the form of a liquid, a solution, a suspension or an emulsion wherein the barrel contains the fluid medium in a portion of the barrel and contains a gaseous medium in another portion of the barrel. After the barrel has been filled, a sterile plug is inserted through the proximal end of the barrel to close the proximal end. After pressing the plug into the barrel, the barrel is vented through a tube extending past the plug so that only the liquid medium is within the barrel. In accordance with one embodiment of the production process, the barrel is filled first through the open proximal end and then subsequently through a tube which extends past the plug.

18 Claims, 2 Drawing Sheets

TERMINAL STERILIZATION PROCESS FOR FILLED SYRINGES UNDER AN AUXILIARY PRESSURE

The invention relates to a process for filling and sealing syringes that are terminally sterilized. In this case, particular emphasis is placed on ensuring a problem-free insertion of the plunger into the syringe body. These syringes are provided preferably for the use of injectable diagnostic agents, especially contrast media that are injected into, for example, blood vessels, organs, organ parts, cavities, and other vessels or exert an imaging action there.

Publication EP 0 227 401 describes a process for the production of a filled, terminally sterilized plastic syringe. The syringe has a cylinder with a distal end with a syringe outlet piece. The syringe outlet piece is sealed by a closure. After being filled, the syringe is sealed with a flexible rubber plug, which can slide in the cylinder. The process begins with waste particles or other contaminants being removed from the closure and the plunger. Microbial contaminants on the closure and the plunger are destroyed. The cylinder is washed with a considerable number of water jets to remove pyrogens and waste particles. Then, silicone oil is applied to the inner wall of the syringe. The closure is then slipped onto the syringe outlet piece. The contrast medium is loaded into the syringe via the proximal end of the syringe. The syringe is then sealed with the plug. This assembled and filled syringe is sterilized in an autoclave. In this case, in addition to the usual autoclave pressure, an additional supporting pressure is generated in the autoclave. As a result, the pressure on the outer surface of the syringe is equal to or greater than the pressure on the inner surface of the syringe.

Terminal sterilization of prefilled cartridge-needle units is known from the publication by Venten and Hoppert (E. Venten and J. Hoppert (1978) Pharm. Ind. Vol. 40, No. 6, pages 665 to 671). The cartridge-needle units, which have a plug at the proximal end, are filled distally via the rolled edge. The rolled edge is then sealed with a sealing disk, whereby a flange cap secures the sealing disk to the rolled edge (M. Junga (1973) Pharm. Ind. Vol. 35, No. 11a, pages 824 to 829). The prefilled cartridge-needle units are then moved to an autoclave, which can be adjusted with respect to temperature and pressure. Thus, the sealing disk is not separated from the cartridge-needle unit, and supporting pressure is produced in the autoclave. The supporting pressure is built up by an additional gas. This makes it possible to keep the pressure on the inside of the sealing disk approximately equal to the pressure on the outside of the sealing disk. For this purpose, movement of the plunger that is already used is also avoided. With proper adjustment, it is even possible to sterilize terminally two-chamber cartridge-needle units that are filled with two solutions, without an unreliable plug movement or sealing disk leak occurring.

EP 0 553 926 describes a terminal sterilization process for prefilled syringes, in which no autoclave is used; rather only a pressure-resistant sterilization chamber is used. The distal or proximal filled syringe is introduced into said sterilization chamber. The chamber is heated using fuel gas. At the same time, this fuel gas also provides pressure that is to offset the increase in pressure in the syringe. To prevent the evaporation of liquid that can penetrate the plastic, steam is to be introduced optionally in addition to fuel gas. It is described in the industrial property right that the same reliability with respect to sterilization is to be achieved as in autoclaving.

WO 95/12482 describes a process for the production of prefilled plastic syringes that are filled with a contrast medium. The syringes consist of a cylinder and a syringe outlet piece at the distal end, which is prepared for a cannula attachment. In addition, the syringe comprises a plug, which can slide in the cylinder. It seals the proximal end of the syringe. The syringe has been produced according to a process that results in pyrogen-free objects. Also, particles are no longer present. The syringe is filled via the proximal end, in which case the syringe outlet piece is sealed with a closure. The filled syringe is then sealed with the plug. The particle status of the spaces corresponds to the conditions of class 100. After the syringe parts come out of the die, they are blown off with gas to remove particles. The syringe is then washed. The syringe is then sterilized, so that it can be further processed, stored, or transported, as desired.

The plug of the syringes that are described above usually consists of an elastic rubber material. This plug is pushed into the inside of the already prefilled syringe body. For this purpose, it is necessary that a compression device that is produced expressly for this purpose compress the plug with respect to the cylinder wall. This causes no problem in the case of elastic rubber material. In addition to this very flexible rubber material, plugs that have a modulus of elasticity that is considerably larger than the modulus of elasticity of rubber are also suitable.

The object is to offer a syringe that is prefilled with a medium and is sealed after filling is completed, whereby the medium is permanently present in the syringe without loss of quality. In this case, in particular the residual air volume in the syringe is to be small enough to prevent any impediment from occurring during sterilization and administration. In this case, the plug is to have a higher modulus of elasticity than conventional rubber plugs.

The object is achieved by a production process for a prefilled, sterile syringe that is made of glass or plastic or a mixture of glass and plastic, as well as a glass syringe with a plastic film that is connected to it and a plastic syringe with a glass coating that is connected to it;
in this case, the syringe comprises
  a cylindrical syringe body with a sealable proximal end,
    a sealable distal end, with an inner wall and an outer wall,
  a syringe outlet piece at the distal end,
  a closure that seals the syringe outlet piece,
  a plug that can slide in the syringe body,
    in this case, the plug can be moved by a plunger, and
  a fluid medium and a gaseous medium,
    whereby the fluid medium is a liquid, a solution, a suspension, or an emulsion,
whereby the process comprises the following steps:
  Provision of the syringe body, from which germs, pyrogens and/or endotoxins are removed and which has a low content of particles,
  provision of the closure, from which germs, pyrogens and/or endotoxins are removed and which has a low content of particles,
  provision of the plug, from which germs, pyrogens and/or endotoxins are removed and which has a low content of particles,
  application of a lubricant,
  sealing of the distal end by the closure of the syringe outlet piece
  filling the syringe via the proximal end and inserting the plug through the proximal end,
  removing the air from the syringe by at least partial compression of the plug, whereby the contact area of the plug, which is in contact with the inner wall of the syringe body, is pressed in using a compression device, in this case the inner compression device that has at least one channel comprises at least one needle, a lance, a rod, a cylinder wall part or a prism wall part, and thermal sterilization in a sterilization chamber.

The process according to the invention is advantageous for all plug shapes and plug materials. The residual air in the filled syringe is kept to a minimum by this procedure. This has considerable advantages both in the case of a terminal sterilization and in the later administration. Air residues are always a nuisance when the contents of a syringe are to be injected in a patient. In the case of thermal sterilization, residual air in a syringe always results in increased pressure, whereby the sum consists of the partial pressure, which is attributed to the water vapor, and a gas partial pressure, which is produced by the residual volume of the gas that is found in the syringe.

Plugs for syringes can be made of very different materials. In the case of small volumes, the rubber-elastic plugs that are mentioned above are preferred. If, however, higher pressures are used on the plug during administration, undesirable deformations of the rubber-elastic plug can result. Plugs that are made of a less elastic material are therefore preferred. More preferred are plugs that have a relatively unelastic, plate-shaped core and that are made of a plastic with a coating that is made of rubber-elastic material. Such plugs can be designed in two pieces. The solid core consists of a cylindrical disk, which fits into a rubber-elastic plug that is hollowed-out inside. The rubber-elastic part has a relatively thin wall thickness, which ensures a tight fit of the plug relative to the inner wall of the syringe. It is disadvantageous, however, that they can no longer be used for rubber plugs like otherwise commonly used compression devices. Either the compression pressures that are used are no longer adequate, or no more reversible deformations of the plug occur.

The term syringe comprises the terms cartridge (large-volume syringe with at least 100 ml of volume), ampoule syringes, disposable syringes, disposable cartridge-needle units, one-way syringes, injection ampoules, cartridge-needle units, ampoules that are ready for spraying, barrel ampoules, and emergency syringes.

Glass syringes and plastic syringes are described in detail in the publication by M. Junga. A mixture of glass and plastic is presented in WO 96/00098 (date of application 6/23/1995).

Plastics are presented in more detail in Römpp-Chemie-Lexikon [Römpp Chemistry Dictionary], publishers Jürgen Falbe and Manfred Regitz, 9th Edition, Stuttgart, 1990 on pages 2398 ff. Preferred are COC, TPX, PP and polymethyl pentene (COC=cycloolefin copolymer). These plastics are especially suitable for use in prefilled, terminally sterilized syringes since their high melting points of at least 130° C. allow steam sterilization according to the standard process at 121° C. Moreover, the optical properties are adequate to allow a visual inspection according to pharmacopeia.

Prism wall parts or cylinder wall parts are essentially large-area structures that can press together and guide the plug as a lance and rod. They can optionally have an irregular outer shape. The function of compressing the rubber plugs and in this case shaping them in an essentially complementary way at least partially to rubber plugs to exert as uniform a pressure as possible on the plug is important.

The terms proximal and distal are defined from the standpoint of the attending physician. At the distal end is the syringe outlet piece to which, for example, the cannula or a hose that leads to a duct is connected. At the proximal end is the plug that presses the medium through the distal end during administration. The plug can be moved manually or else mechanically. The term plug also comprises plungers. For manual actuation of the syringe, it is helpful to the operator if the syringe has finger holders at the proximal end. In this case, the finger holders usually have at least one surface as a block for the index finger and the middle finger, whereby the surface of the finger holder is basically perpendicular to the axis of the syringe cylinder. In the case of mechanical pumping devices, various models are known. A syringe then preferably carries one or more device holders, preferably at the proximal end. Such a mechanical pump is described especially well in publication EP 0 584 531 (date of application Jul. 21, 1993). Also, mixed devices made of finger holders and device holders are possible.

The syringes are usually rotationally symmetrical; only the finger holders and device holders and occasionally also the syringe outlet piece deviate from symmetry. Thus, the syringe outlet piece can be arranged eccentrically. Especially preferred is the Luer lock since in the administration of contrast media it is used exclusively when mechanical pumping devices are used. Also, in the case of manual administration, the Luer lock and the hose that is connected to it are avoided, so that intentional motions by the physician are not transferred directly to the cannula. In addition, the simple Luer nozzle and also the record nozzle are known. The proximal and distal ends of the syringe must be sealable. The distal end is sealed by a closure, which can be placed on the syringe outlet piece. In the present invention, the syringe outlet piece comprises the cover of the syringe cylinder. In addition, the syringe outlet piece comprises a tube, which has the needle or the hose, an endpiece, which is in contact with the needle or the hose, and a cylinder that is threaded on the inside, whereby the cylinder surrounds the endpiece and is threaded for, for example, a Luer lock. In this case, the syringe outlet piece may be one-piece or multiple-piece. The cover can be arched, flat, or pyramid-shaped. Mixed devices are also conceivable. The plug seals the proximal end of the syringe. It must be able to slide in the cylinder and must reliably shield the medium from the environment. It is to be as gas-tight and liquid-tight as possible. Also, temperature fluctuations must be tolerated without disruption of operation. Usually, the plug is not provided with a separate plunger when the syringes are mechanically emptied. Rather, a plunger that is part of the pumping device engages in a closure inside the plug, so that the plug can move with ease (cf. publication EP 0 584 531). Even in the mechanical administration, the plug can be made of a material that is less elastic than the otherwise commonly used rubber material. Such plugs are necessary, since the pressure that is caused by the pumping devices results in deformation of the otherwise commonly used rubber material. The other commonly used rubber material evades the stresses that occur, and undesirable leaks between the rubber plug and the inner wall of the syringe occur. Such mistakes can jeopardize the entire method of administration to a large extent. The volume and also the associated pressure are no longer clearly defined. This process is especially preferred in the case of plugs that are no longer designed in one piece. Such plugs have a cylindrical disk that is made of a relatively less elastic material and a sealing part that is turned over above it, which is produced from, for example, a rubber-elastic material. When this two-part plug or a plug with similarly less elastic function is used, the problem arises of compressing the rubber plug with conventional compression devices. As a result, an undesirable residual volume of air remains in the syringe. This air can no longer easily escape when the plug is inserted into the syringe body.

A production process in which the filling of the syringe and the insertion of the plug are timed so that the plug is used after the filling is completed is preferred.

Another preferred production process consists in the fact that the filling of the syringe and the use of the plug is timed so that the plug is used before the filling, whereby the syringe is filled by the compression device, in this case, the compression device comprises at least one channel for filling and one channel for removing the air.

A production process is also possible in which a partial filling is done in such a way that the plug is used after the filling is completed, and residual filling is done in such a way that the plug is used before the residual filling, whereby the syringe is filled by the compression device in the case of residual filling, and in this case the compression device comprises at least one channel for filling and one channel for removing the air.

A production process in which the compression device consists of at least one needle for filling and one needle for removing the air is also preferred. More preferred is a compression device that has two needles each for filling and for removing the air.

More preferred is a production process, whereby the needles are arranged on a holding device, and the points where the needles are inserted lie essentially on a circular line that is located above the contact area of the plug. More preferred is a holding device that is designed in a circular or semicircular manner. Especially preferred is a production process in which the holding device comprises at least one supply line. In addition, it is also possible to work with at least two supply lines, whereby one supply line is used for filling and the other for removing the air.

Further preferred is a production process in which a guide ring, whose plane runs parallel to the plane of the holding device, is arranged between syringe and holding device. Such a guide ring makes it easy to insert the needles securely into the syringe body. Tilting or jamming is thus virtually impossible. More preferred is a production process in which the needle deviates by an angle of 0.5 to 2°, more preferably by 1° from the axis of the syringe body, whereby the part of the needle that lies closest to the distal end of the syringe points inward.

To achieve reliable filling, it is useful to determine the filling level of a syringe body. For this purpose, a production process according to the invention in which the degree of filling is determined by a sensor is advantageous. A capacitive sensor is preferred. The use of such sensors in fillings has proven its value especially well, since in this case, it is advantageous that a contact-free and reproducible filling level measurement is possible, without in this case the syringe or its contents being affected.

Preferred is a production process, whereby the sterilization chamber is an autoclave or sterilizer, with steam, hot air and/or microwaves. Such sterilization chambers are described in detail in the cited prior art. The additional supporting pressure, which can be built up in the sterilization chamber, is especially advantageous. Most preferred in this case is a production process, whereby a supporting pressure is built up by a gas in the sterilization chamber, whereby the pressure on the outer surface of the syringe is equal to, greater than or less than the pressure on the inner surface of the syringe.

The medium in the filled syringe is a mixture that consists of a fluid medium and at least one gas. The medium may be a liquid, a solution, a suspension, or an emulsion. These manifestations are described in W. Schröter et al., (1987) Chemie; Fakten und Gesetze [Chemistry; Facts and Laws], 14th Edition, Leipzig on pages 23 ff. A fluid medium that is a contrast medium is preferred. Sterile and pure production processes are described in DAB 1996 or Ph. EUR.

Lubricants are used to ensure that the plug can be moved without major expenditure of force inside the cylinder. Preferred is silicone oil that has the following properties: viscosity of at least 1000 cST; grade: medical grade.

So that the plug does not travel inside the cylinder during sterilization, it can be advantageous if the plug is fixed during sterilization. As a result, a pressure differential can be built up between the volume in the syringe and the volume around the syringe. Such a fixing of the plug is described in detail in the French Patent with publication number 2,258,866, which was filed on Jan. 30, 1974.

A preferred embodiment according to the invention is pictured by way of example in the drawings.

Figure 1:
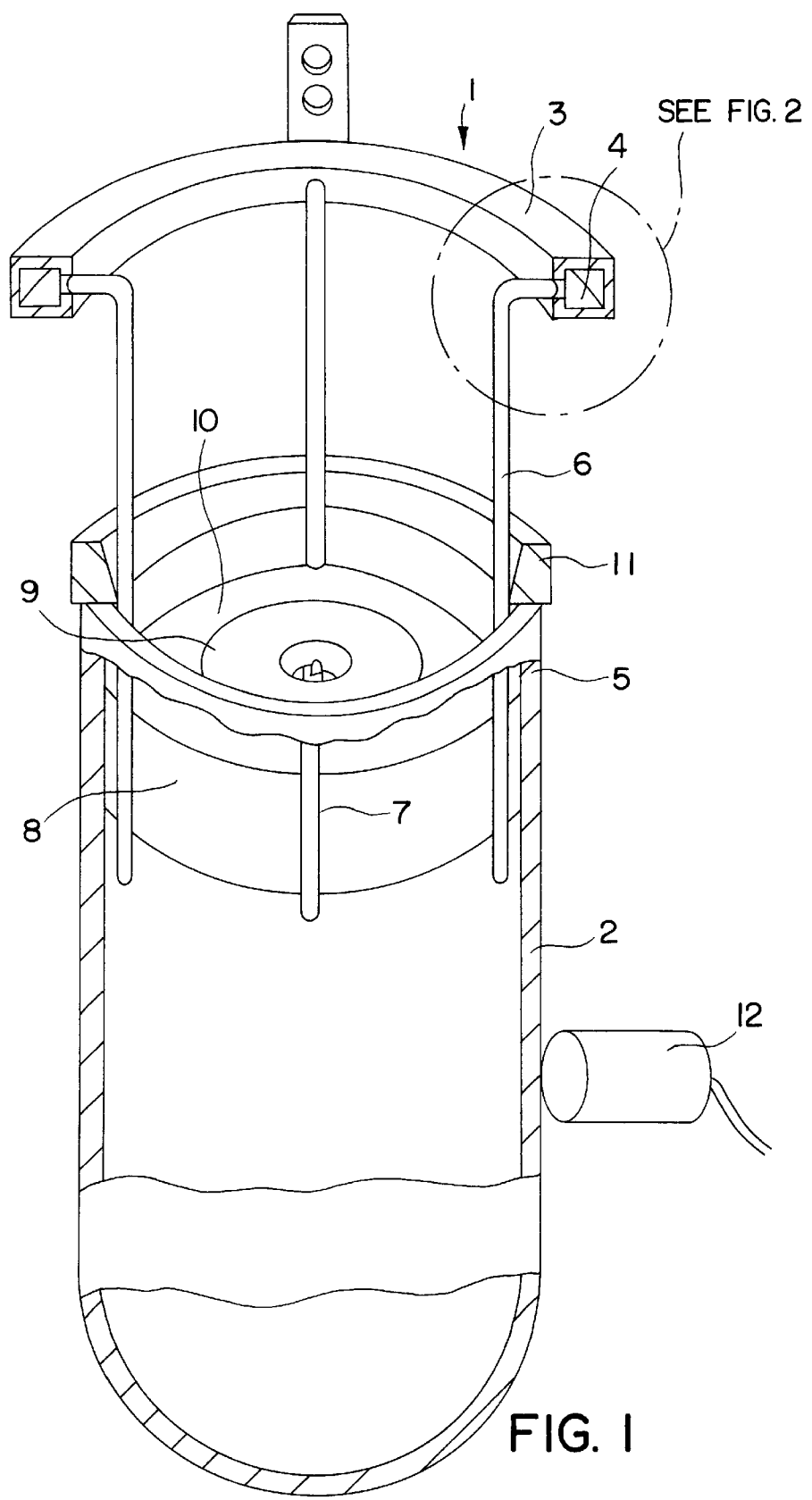
FIG. 1 shows a perspective view through a syringe body in which is located a plug that is inserted through a compression device.

A compression device 1, which projects into a syringe body 2 of a syringe, is shown in FIG. 1. Compression device 1 comprises a holding device 3, which is arranged in a circular manner and which comprises a supply line 4. Holding device 3 has a rectangular cross-section. The center of the circular ring of holding device 3 coincides with the axis of the syringe body. Holding device 3 is arranged outside of proximal end 5 of syringe body 2. Needles 6 that are designed in an L shape extend from holding device 3 in the direction of syringe body or barrel 2, whereby the long leg of needles 6 runs parallel to the axis of the syringe body. Needles 6 touch inner wall 7 of syringe body 2 with the long leg. The long legs of needles 6 also touch plug or barrel 8, which is made in two pieces. Plug 8 has a solid core 9, which is not very elastic. Core 9 has essentially the shape of a disk, which in the center has a hole in which a plunger that is not pictured in the drawing can be attached. Core 9 of plug 8 is surrounded by a plug casing outer portion 10, which almost completely encompasses core 9. Only in the proximally pointing part of plunger 8 does casing 10 not encompass core 9. Casing outer portion 10 is produced from a rubber-elastic material. It provides for the seal against inner wall 7 of syringe body or barrel 2. Plug 8 is designed in a pyramid shape on its distal end. It has a shape that is complementary to the syringe outlet piece at the distal end.

A guide ring 11, which touches the long leg of tubes in the form of needles 6 on the outside, is arranged below holding device 3. Guide ring 11 adjoins proximal end 5 of syringe body or barrel 2. The guide ring has a cross-section that is built-up conically, whereby it has a wider cross-section in the distal range than in the proximal range.

When a syringe is filled, guide ring 11 is first put on the proximal end of the syringe body. Then, holding device 3, on which needles 6 are located, travels from outside of the syringe in the direction of the syringe body. In this case, the tubes in the form of needles 6 have already grasped plug 8 and pressed rubber-elastic casing 10 slightly inward. Holding device 3 now inserts the plug, including needles 6, through guide ring 11 into syringe body 2. In this case, air is removed from the syringe body at the same time by the channels in the needles. As desired, in this case the syringe can be filled ahead of time with the liquid medium or only after the plug is inserted. It is essential in the procedure to insert plug 8 into syringe body or barrel 2 in such a way that residual air between plug 8 and the liquid is removed from syringe body or barrel 2.

Figure 2:
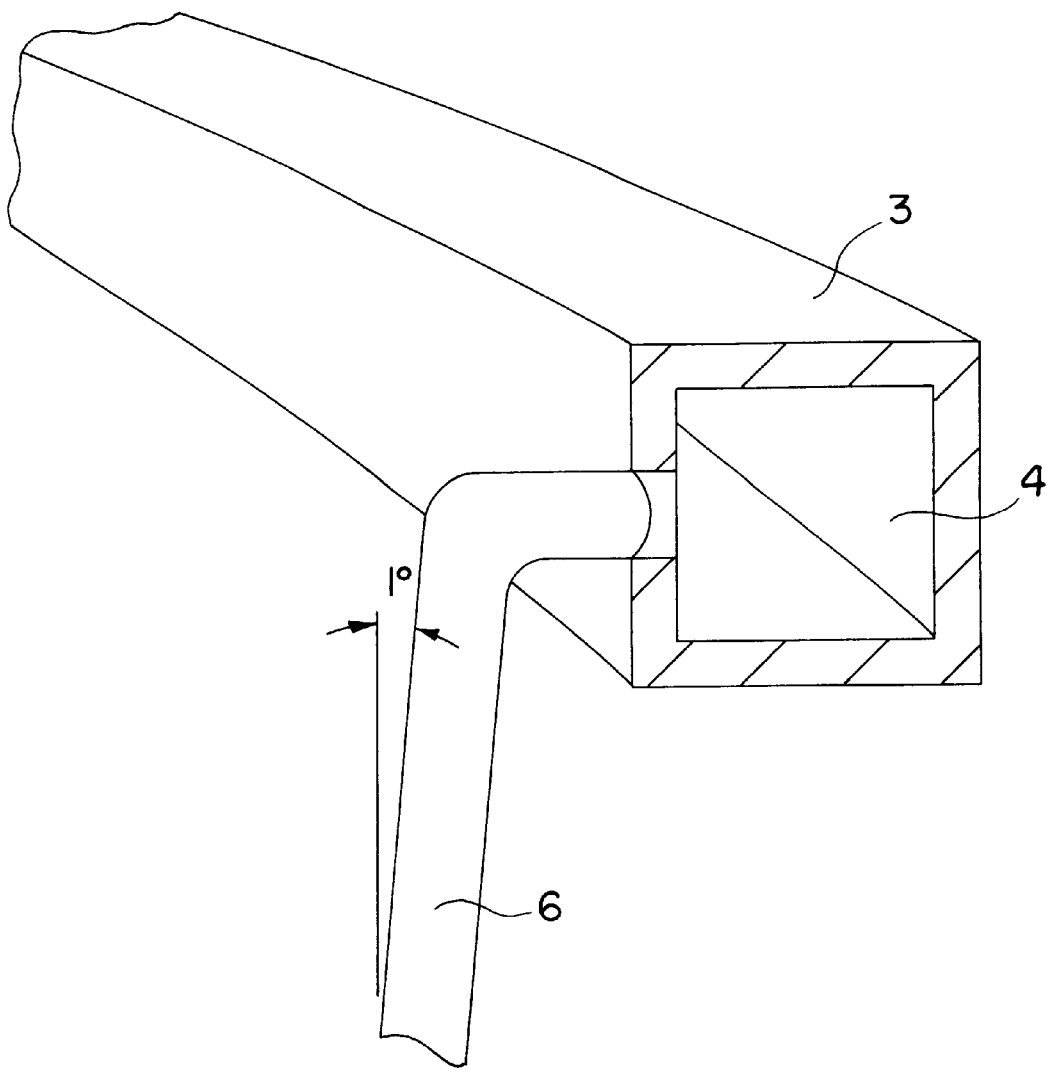
FIG. 2 shows a detail view of a needle leaving the holding device.

FIG. 2 shows in detail holding device 3, from which a needle leaves. In this case, it is especially clear that the long leg of needle 6 has an angle of 1° compared to the axis of the syringe body. Supply line 4 can also be eliminated. Needles 6 must then be guided outside by holding device 3. There, the needles would be connected individually to the fill-drain line.

A sensor 12 that can record the filling height during filling is also pictured in FIG. 1. This sensor 12 is built as a capacity sensor.

| Legend: |
| --- |
| 1 Compression device |
| 2 Syringe body |
| 3 Holding device |
| 4 Supply line |
| 5 Proximal end |
| 6 Needle |
| 7 Inner wall |
| 8 Plug |
| 9 Core |
| 10 Casing |
| 11 Guide ring |
| 12 Sensor |

What is claimed is:

1. A production process for a prefilled, sterile syringe comprising:
   providing a sterilized syringe barrel having sealable proximal and sealable distal ends, the proximal end being open and the distal being adapted for coupling with a syringe outlet piece, the barrel having an inner wall surface;
   closing the distal end of the barrel;
   filling the barrel through the proximal end while the proximal end is open with a fluid medium in the form of a liquid, a solution, a suspension or an emulsion, wherein the barrel contains the fluid medium in one portion of the barrel and a gaseous medium in another portion of the barrel;
   after filling the barrel, inserting a sterile plug through the proximal end of the barrel to close the proximal end, the sterile plug having at least an outer portion which is elastic; and
   while pressing the plug into the barrel, venting the gaseous medium through a tube extending past the plug so that only the liquid medium is within the barrel.

2. A production process according to claim 1, wherein an array of tubes are arranged on a holding device, and points where the tubes are mounted on the holding device lie essentially on a circular line that is located above the plug.

3. A production process according to claim 2, wherein the tube deviates by an angle of 0.5° to 2° from the axis of the barrel, whereby the part of needle (6) that lies closest to the distal end of the syringe points inward.

4. A production process according to claim 1, whereby a sterilization chamber in the form of an autoclave or sterilizer, with steam, hot air and/or microwaves is provided to sterilize the syringe.

5. A production process according to claim 1 wherein supporting pressure is built up around the syringe by a gas in the sterilization chamber, whereby the pressure on the outer surface of the syringe is equal to, greater than, or less than the pressure on the inner surface of the syringe.

6. A production process according to claim 1, wherein the syringe is selected from devices comprising: cartridges, ampoule syringes, disposable syringes, disposable cartridge-needle units, one-way cartridge-needle units, one-way syringes, injection ampoules, cartridge-needle units, ampoules that are ready for spraying, barrel ampoules, and emergency syringes.

7. A production process according to claim 1, wherein the plastic of polyolefins comprising the barrel is selected from the group consisting of COC, TPX, polymethyl pentene, and PP.

8. A production process according to claim 1, wherein the barrel of the syringe has a Luer lock at the distal end.

9. A production process according to claim 1, wherein the medium in the filled syringe is a mixture that consists of a fluid medium and at least one gas.

10. A production process according to claim 1, wherein the fluid medium is a contrast medium.

11. A production process according to claim 1, wherein the plug is fixed within the barrel during sterilization.

12. The production process of claim 1, wherein the tube extends between the plug and the inner wall surface of the barrel.

13. The production process of claim 12, wherein there are at least two tubes, one of which is used to add residual fluid medium to the barrel and the other of which is used to vent residual gaseous medium from the barrel as the residual gaseous medium is displaced by the residual fluid medium.

14. The production process of claim 13, wherein the tubes extend from a support and are passed through a guide ring disposed at the proximal end of the barrel.

15. The production process of claim 14, wherein the filling height is monitored by an external sensor.

16. A production process according to claim 15, whereby the sensor is a capacitive sensor.

17. The production process of claim 1, wherein the filling height is monitored by an external sensor.

18. The production process of claim 1, wherein lubricant is disposed between the plug and inner wall surface of the barrel.

* * * * *